United States Patent
Riley et al.

(10) Patent No.: US 9,789,057 B2
(45) Date of Patent: Oct. 17, 2017

(54) PHARMACEUTICAL DELIVERY SYSTEM

(75) Inventors: Thomas C. Riley, Manchester, MO (US); R. Saul Levinson, Chesterfield, MO (US); Robert C. Cuca, Glen Carbon, IL (US); Elio Mariani, Chesterfield, MO (US)

(73) Assignee: Perrigo Pharma International Designated Activity Company, Dublin (IE)

( * ) Notice: Subject to any disclaimer, the term of this patent is extended or adjusted under 35 U.S.C. 154(b) by 803 days.

(21) Appl. No.: 13/555,472

(22) Filed: Jul. 23, 2012

(65) Prior Publication Data

US 2013/0102548 A1  Apr. 25, 2013

Related U.S. Application Data

(63) Continuation of application No. 10/944,416, filed on Sep. 20, 2004, now abandoned.

(60) Provisional application No. 60/507,138, filed on Oct. 1, 2003, provisional application No. 60/504,017, filed on Sep. 19, 2003.

(51) Int. Cl.
   *A61K 9/00* (2006.01)

(52) U.S. Cl.
   CPC .......... *A61K 9/0036* (2013.01); *A61K 9/0034* (2013.01)

(58) Field of Classification Search
   None
   See application file for complete search history.

(56) References Cited

U.S. PATENT DOCUMENTS

| | | | |
|---|---|---|---|
| 4,018,918 A | 4/1977 | Ayer et al. | |
| 4,342,741 A | 8/1982 | Aoki | |
| 4,348,415 A | 9/1982 | Tsutsumi et al. | |
| 4,446,051 A | 5/1984 | Berthod et al. | |
| 4,551,148 A | 11/1985 | Riley, Jr. et al. | |
| 4,683,243 A | 7/1987 | Sunshine et al. | |
| 4,803,066 A | 2/1989 | Edwards | |
| 4,895,934 A | 1/1990 | Matier et al. | |
| 4,943,389 A | 7/1990 | Weete et al. | |
| 5,008,037 A | 4/1991 | Weete et al. | |
| 5,055,303 A | 10/1991 | Riley, Jr. | |
| 5,085,856 A | 2/1992 | Dunphy et al. | |
| 5,143,934 A | 9/1992 | Lading et al. | |
| 5,266,329 A | 11/1993 | Riley, Jr. | |
| 5,527,534 A | 6/1996 | Myhling | |
| 5,531,703 A | 7/1996 | Skwarek et al. | |
| 5,536,743 A | 7/1996 | Borgman | |
| 5,554,380 A | 9/1996 | Cuca et al. | |
| 5,599,528 A | 2/1997 | Igaki | |
| 5,618,522 A | 4/1997 | Kaleta et al. | |
| 5,814,330 A | 9/1998 | Putteman et al. | |
| 5,888,523 A | 3/1999 | Galask et al. | |
| 5,948,825 A | 9/1999 | Takahashi et al. | |
| 5,985,319 A | 11/1999 | Embil et al. | |
| 5,993,856 A | 11/1999 | Ragavan et al. | |
| 6,004,566 A | 12/1999 | Friedman et al. | |
| 6,022,547 A | 2/2000 | Herb et al. | |
| 6,113,921 A | 9/2000 | Friedman et al. | |
| 6,140,355 A | 10/2000 | Egidio et al. | |
| 6,150,400 A | 11/2000 | Nyirjesy et al. | |
| 6,228,383 B1 | 5/2001 | Hansen et al. | |
| 6,262,126 B1 | 7/2001 | Meinert | |
| 6,267,985 B1 | 7/2001 | Chen et al. | |
| 6,277,370 B1 | 8/2001 | Cavaliere Ved. Vesely et al. | |
| 6,284,281 B1 | 9/2001 | Chevalier et al. | |
| 6,316,011 B1 | 11/2001 | Ron et al. | |
| 6,316,433 B1 | 11/2001 | Rose et al. | |
| 6,387,383 B1 | 5/2002 | Dow et al. | |
| 6,416,778 B1 | 7/2002 | Ragavan et al. | |
| 6,416,779 B1 | 7/2002 | D'Augustine et al. | |
| 6,419,938 B1 | 7/2002 | Riedel et al. | |
| 6,423,307 B2 | 7/2002 | Saettone et al. | |
| 6,479,545 B1 | 11/2002 | Levinson et al. | |
| 6,495,157 B1 | 12/2002 | Pena et al. | |
| 6,803,420 B2 | 10/2004 | Cleary et al. | |

(Continued)

FOREIGN PATENT DOCUMENTS

DE    100 15 463 A1    10/2001
DE    10015463 A1 *   10/2001

(Continued)

OTHER PUBLICATIONS

Ahmed-Jushuf, I. H., et al., "The Treatment of Bacterial Vaginosis with a 3 Day Course of 2% Clindamycin Cream: Results of a Multicentre, Double Blind, Placebo Controlled Trial," Genitourinary Medicine, Aug. 1995, pp. 254-256, vol. 71, No. 4.

Aroutcheva, A., et al., "The Inhibitory Effect of Clindamycin on Lactobacillus in vitro," Infectious Diseases in Obstetrics and Gynecology, 2001, pp. 239-244, vol. 9, No. 4.

Amsel, R., et al., "Nonspecific Vaginitis. Diagnostic Criteria and Microbial and Epidemiologic Associations," The Journal of American Medicine, Jan. 1983, pp. 14-22, vol. 74, No. 1.

(Continued)

*Primary Examiner* — Robert A Wax
*Assistant Examiner* — Caralynne Helm
(74) *Attorney, Agent, or Firm* — Honigman Miller Schwartz and Cohn LLP; Kathryn D. Doyle, Esq.; Jonathan P. O'Brien

(57) ABSTRACT

A pharmaceutical formulation to treat vaginal conditions in a human patient comprises:
  at least one active agent;
  a modified release dosage form which provides extended release of the anti-infective agent upon vaginal administration to the patient; and
  wherein the formulation, when containing a total dose of the anti-infective agent of about 25 μg to about 500 mg based on the active agent will produce a plasma concentration versus time curve (ng/mL versus hours) having an area under the curve (AUC) of less than about 600 ng/mL·hr.

17 Claims, 4 Drawing Sheets

(56) References Cited

U.S. PATENT DOCUMENTS

| | | | |
|---|---|---|---|
| 6,899,890 | B2 | 5/2005 | Kirschner et al. |
| 2002/0094341 | A1 | 7/2002 | Jorgensen et al. |
| 2002/0114847 | A1 | 8/2002 | Peshoff |
| 2002/0188264 | A1 | 12/2002 | Knuth et al. |
| 2002/0197314 | A1 | 12/2002 | Rudnic et al. |
| 2003/0083286 | A1 | 5/2003 | Teng et al. |
| 2003/0091540 | A1 | 5/2003 | Ahmad et al. |
| 2003/0091642 | A1 | 5/2003 | Auzerie |
| 2003/0152598 | A1 | 8/2003 | Heidenfelder et al. |
| 2003/0180366 | A1 | 9/2003 | Kirschner et al. |
| 2003/0219465 | A1 | 11/2003 | Gidwani et al. |
| 2003/0219472 | A1 | 11/2003 | Pauletti et al. |
| 2003/0225034 | A1 | 12/2003 | Floros et al. |
| 2004/0121003 | A1 | 6/2004 | Chickering, III et al. |
| 2004/0151774 | A1 | 8/2004 | Pauletti et al. |
| 2004/0167223 | A1 | 8/2004 | Popp |
| 2004/0234606 | A1 | 11/2004 | Levine et al. |
| 2005/0095245 | A1 | 5/2005 | Riley et al. |
| 2005/0118210 | A1 | 6/2005 | Kachi et al. |

FOREIGN PATENT DOCUMENTS

| | | |
|---|---|---|
| EP | 0 404 376 A2 | 12/1990 |
| EP | 1 110 541 A1 | 6/2001 |
| EP | 1 652 535 A1 | 5/2006 |
| GB | 1 525 120 | 9/1978 |
| JP | 4-500365 A | 1/1992 |
| JP | 07-291856 A | 11/1995 |
| JP | 2001-151662 A | 6/2001 |
| JP | 2003-519095 A | 6/2003 |
| JP | 2003-212747 A | 7/2003 |
| WO | 87/02576 | 5/1987 |
| WO | 87/04593 | 8/1987 |
| WO | 90/14832 A1 | 12/1990 |
| WO | 92/18101 | 10/1992 |
| WO | 95/07171 | 3/1995 |
| WO | 97/44032 A1 | 11/1997 |
| WO | 01/10407 A1 | 2/2001 |
| WO | 02/03896 A1 | 1/2002 |
| WO | 03/000224 A1 | 1/2003 |
| WO | 03/079981 A2 | 10/2003 |
| WO | 2004/096151 A2 | 11/2004 |
| WO | 2005/013906 A2 | 2/2005 |
| WO | 2005/087270 A1 | 9/2005 |

OTHER PUBLICATIONS

Bollert, J. A., et al., "Teratogenicity and Neonatal Toxicity of Clindamycin 2-Phosphate in Laboratory Animals," Toxicology and Applied Pharmacology, Feb. 1974, pp. 322-329, vol. 27, No. 2.
Borin, M. T., et al., "Absorption of Clindamycin After Intravaginal Application of Clindamycin Phosphate 2% Cream," The Journal of Antimicrobial Chemotherapy, Jun. 1995, pp. 833-841, vol. 35, No. 6.
Borin, M. T., et a., "Systemic Absorption of Clindamycin After Intravaginal Administration of Clindamycin Phosphate Ovule or Cream," Journal of Clinical Pharmacology, Aug. 1999, pp. 805-810, vol. 39, No. 8.
Brown, D., et al., "Butoconazole Nitrate 2% for Vulvovaginal Candidiasis," The Journal of Reproductive Medicine, Nov. 1999, pp. 933-938, vol. 44, No. 11.
Cleocin(R) Vaginal Cream 2% Package Insert.
Cleocin(R) Vaginal Cream, Physicians Desk Reference, 1999, pp. 2462-2464.
Esposito, E., et al., "Amphiphilic Association Systems for Amphotericin B Delivery," International Journal of Pharmaceutics, Jul. 24, 2003, pp. 249-260, vol. 260, No. 2.
Ferris, D. G., et al., "Over-The-Counter Antifungal Drug Misuse Associated with Patient-Diagnosed Vulvovaginal Candidiasis," Obstetrics and Gynecology, Mar. 2002, pp. 419-425, vol. 99, No. 3.
Ferris, D. G., et al., "Treatment of Bacterial Vaginosis: A Comparison of Oral Metronidazole, Metronidazole Vaginal Gel, and Clindamycin Vaginal Cream," Abstract, The Journal of Family Practice, Nov. 1995, pp. 443-449, vol. 41, No. 5.
Fredricks, D. N., et al., "Molecular Identification of Bacteria Associated with Bacterial Vaginosis," New England Journal of Medicine, Nov. 2005, pp. 1899-1911, vol. 353, No. 18.
Garg, S., et al., "Compendium of Pharmaceutical Excipients for Vaginal Formulations," Pharmaceutical Technology Drug Delivery, 2001, pp. 14-24.
Gavini, E., et al., "Mucoadhesive Vaginal Tablets as Veterinary Delivery System for the Controlled Release of an Antimicrobial Drug, Acriflavine," AAPS PharmSciTech, 2002, 7 Pages, vol. 3, No. 3, Article 20.
Gray, J. E., et al., "The Oral Toxicity of Clindamycin in Laboratory Animals," Toxicology and Applied Pharmacology, Apr. 1972, pp. 516-531, vol. 21, No. 4.
Hextall, A., et al., "Mucosal Concentration and Excretion of Clindamycin by the Human Stomach," The Journal of Antimicrobial Chemotherapy, Mar. 1994, pp. 595-602, vol. 33, No. 3.
Horter, D., et al., "Influence of Physicochemical Properties on Dissolution of Drugs in the Gastrointestinal Tract," Advanced Drug Delivery Reviews, Mar. 2001, pp. 75-87, vol. 46, Nos. 1-3.
International Search Report and Written Opinion for International Patent Application No. PCT/US2004/030672, Mar. 10, 2005, 6 pages.
International Search Report and Written Opinion for International Patent Application No. PCT/US2006/017635, Oct. 12, 2006, 12 pages.
Karasulu, H. Y., et al., "Sustained Release Bioadhesive Effervescent Ketoconazole Microcapsules Tabletted for Vaginal Delivery," Journal of Microencapsulation, 2002, pp. 357-362, vol. 19, No. 3.
Lappin, M. A., et al., "Effect of Butoconazole Nitrate 2% Vaginal Cream and Miconazole Nitrate 2% Vaginal Cream Treatments in Patients with Vulvovaginal Candidiasis," Infectious Diseases in Obstetrics and Gynecology, 1996, pp. 323-328, vol. 4.
McCormack, W. M., et al., "Comparison of Clindamycin Phosphate Vaginal Cream with Triple Sulfonamide Vaginal Cream in the Treatement of Bacterial Vaginosis," Sexually Transmitted Diseases, Oct. 2001, pp. 569-575, vol. 28, No. 10.
Merabet, J., et al., "Advancing Vaginal Drug Delivery," Expert Opinion Drug Delivery, Jul. 2005, pp. 769-777, vol. 2, No. 4.
Merritt, E. W., et al., "Diffusion Apparatus for Skin Penetration," Journal of Controlled Release, 1984, pp. 161-162, vol. 1.
MetroGel-Vaginal(R) 0.75% (Metronidazole Vaginal Gel) Vaginal Gel Package Insert, 10 Pages.
Muli, F., et al., "Use of a Continuous-Culture Biofilm System to Study the Antimicrobial Susceptibilities of Gardnerella vaginalis and Lactobacillus acidophilus," Antimicrobial Agents and Chemotherapy, Jun. 1998, pp. 1428-1432, vol. 42, No. 6.
Nugent, R. P., et al., "Reliability of Diagnosing Bacterial Vaginosis is Improved by a Standardized Method of Gram Stain Interpretation," Journal of Clinical Microbiology, Feb. 1991, pp. 297-301, vol. 29, No. 2.
Osborne, D. W., et al., "Skin Penetration Enhancers Cited in the Technical Literature," Pharmaceutical Technology, Nov. 1997, pp. 58-66.
Ozyurt, E., et al., "Efficacy of 7-Day Treatment with Metronidazole + Miconazole (Neo-Penotran(R))—A Triple-Active Pessary for the Treatment of Single and Mixed Vaginal Infections," International Journal of Gynecology & Obstetrics, 2001, pp. 35-43, vol. 74.
Peters, K., et al., "An Investigation into the Distribution of Lecithins in Nanosuspension Systems Using Low Frequency Dielectric Spectroscopy," Internal Journal of Pharmaceutics, Jul. 5, 1999, pp. 53-61, vol. 184, No. 1.
Redondo-Lopez, V., et al., "Vulvovaginal Candidiasis Complicating Recurrent Bacterial Vaginosis," Sexually Transmitted Diseases, Jan.-Mar. 1990, pp. 51-53, vol. 17, No. 1.
Thompson, D. J., et al., "A Bioadhesive topical Drug Delivery System," Drug Delivery Systems & Sciences, 2002, pp. 17-19, vol. 2, No. 1.
Triggiani, M. et al., "Differential Modulation of Mediator Release from Human Basophils and Mast Cells by Mizolastine," Clinical and Experimental Allergy, 2004, pp. 241-249, vol. 34, No. 2.

(56) References Cited

OTHER PUBLICATIONS

Tucker, S. B., et al., "Comparison of Topical Clindamycin Phosphate, Benzoyl Peroxide, and a Combination of the Two for the Treatment of Acne Vulgaris," The British Journal of Dermatology, Apr. 1984, pp. 487-492, vol. 110, No. 4.

Wang, Y., et al., "Characterization of a Female Controlled Drug Delivery System for Microbicides," Contraception, 2002, pp. 281-287, vol. 66, No. 4.

Weinstein, L. et al., "Vaginal Retention of 2% Butoconazole Nitrate Cream: Comparison of a Standard and a Sustained-Release Preparation," Clinical Therapeutics, Nov.-Dec. 1994, pp. 930-934, vol. 16, No. 6.

Zhang, F., et al., "Rheology and Stability of Phospholipid-Stabilized Emulsions," Journal of the American Oil Chemists' Society, 1997, pp. 869-874, vol. 74, No. 7.

Zolnoun, D. A., et al., "Overnight 5% Lidocaine Ointment for Treatment of Vulvar Vestibulitis," Obstetrics & Gynecology, Jul. 2003, pp. 84-87, vol. 102, No. 1.

\* cited by examiner

FIG. 2

Therapeutic Cure Rate

| | Example 2 formulation (#cured/#evaluable) | Cleocin® (#cured/#evaluable) | 95% CI (Test - Control) | p-value |
|---|---|---|---|---|
| PP Population | 42.1% (53/126) | 45.6% (57/125) | (-15.8, 8.7) | 0.572 |
| mITT Population | 33.0% (73/221) | 37.0% (78/211) | (-12.9, 5.1) | 0.396 |
| ITT Population | 29.7% (78/263) | 30.2% (80/265) | (-8.3, 7.3) | 0.901 |

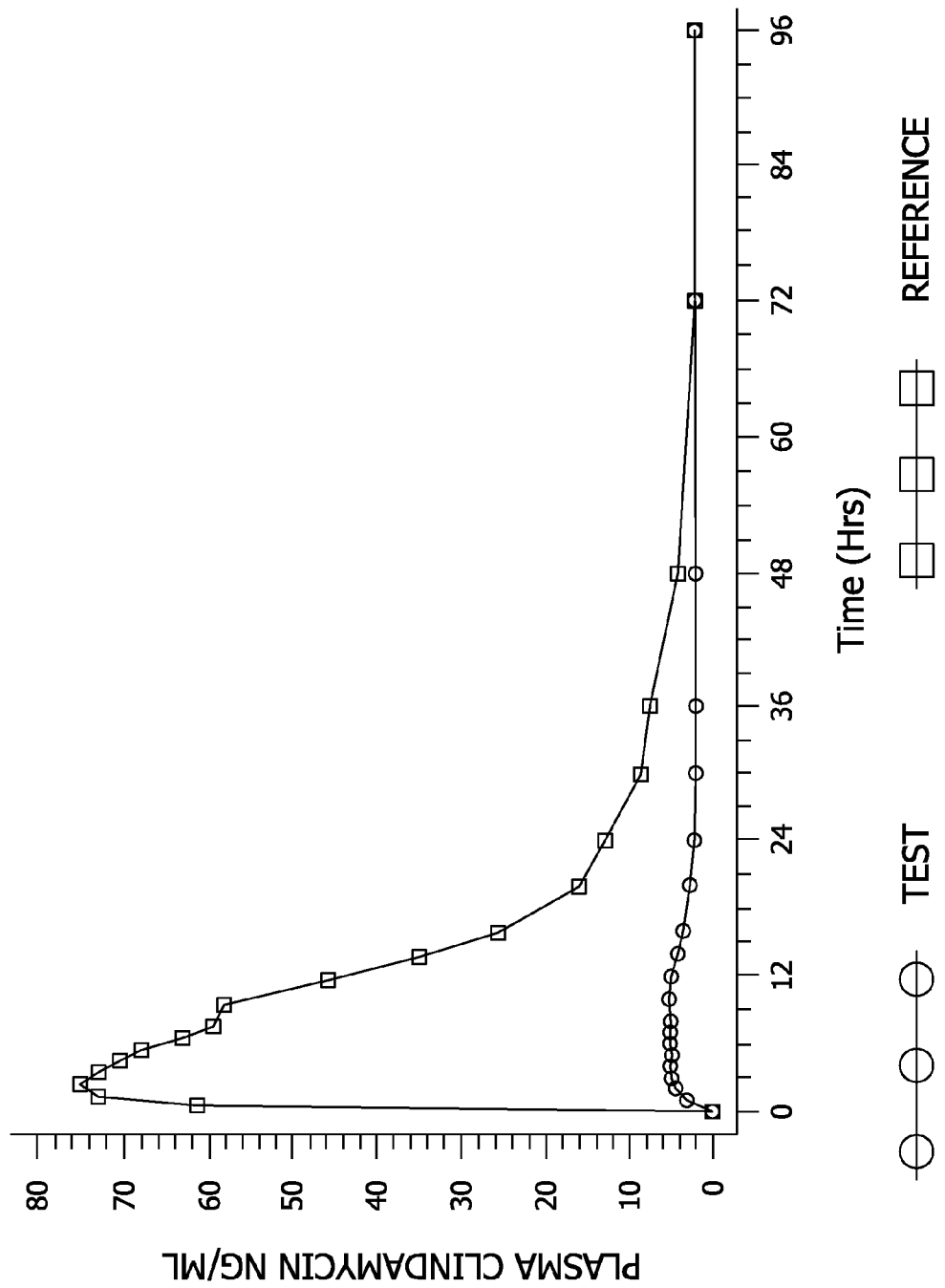

PHARMACEUTICAL DELIVERY SYSTEM

CROSS-REFERENCE TO RELATED APPLICATIONS

This application is a continuation of U.S. patent application Ser. No. 10/944,416 filed Sep. 20, 2004, which claims the benefit of U.S. Provisional Application Ser. No. 60/507,138, filed Oct. 1, 2003, and U.S. Provisional Application Ser. No. 60/504,017, filed Sep. 19, 2003, the entirety of which are herein incorporated by reference.

BACKGROUND OF THE INVENTION

1. Field of the Invention

The present invention is directed to delivery systems, which stabilize surface active therapeutic agents, or those therapeutic agents which obtain surface active properties in a delivery system. These systems are suitable for use in the vaginal cavity, as well as other mucosal cavities of the body. The invention is additionally concerned with preparations demonstrating a modified, controlled, extended or sustained release of the active and/or therapeutic agent and a minimal number of administrations to produce efficacy upon administration of said delivery system.

2. Description of the Related Art

One significant aspect of medicine is the treatment of the female reproductive system for the prevention, treatment, mitigation, diagnosis and cure of diseases and the prevention of conception. Usually, this involves the delivery of active agents to the vaginal cavity and its environs. Systems to affect the delivery of such agents are usually in the form of gels, foams, creams, suppositories and quick dissolving tablets. These delivery systems, regardless of formulation or method of manufacture, have not reliably demonstrated the ability to deliver active agents in a controlled manner with lower systemic absorption within the vaginal cavity for long periods of time, and particularly for 12 hours or longer. This may be attributed to the vaginal cavity environment as well as to the known formulations designed to administer drugs thereto.

The vaginal cavity is subject to conditions rendering it a target for disease and infection; however, as previously noted, it is extremely difficult to deliver an active agent to this area for an extended period of time. The vaginal cavity exhibits an aqueous environment containing secreting glands whose fluids create an acidic pH in the range of 4.5 to 5.5. The environment of the vagina is conducive to the growth of various microbes, such as bacteria, fungi, yeast and other microorganisms since it is warm, moist and dark. It is also the vestibule for menstrual debris and the residual seminal fluid from sexual intercourse. The crevices of the vaginal cavity facilitate the retention of undesirable bacteria, fungi, yeast and other microorganisms, as well as the debris from menstruation and sexual intercourse. The vaginal cavity is also subject to considerable physical deformation, such as during sexual intercourse or during the insertion of tampons.

Active agents having pharmaceutical qualities have been developed and approved for use in the treatment of conditions and diseases of the vaginal cavity and the prevention of conception. These include fungicides, antibiotics, spermicides, etc. Although pharmaceutically active agents have been developed, it has been difficult to achieve optimal potential effectiveness from these agents due to the inadequacy of currently available drug delivery systems. The majority of gels, foams, creams, suppositories and tablets presently used as vaginal delivery systems can breakdown almost immediately following insertion into the vaginal cavity and have minimal bioadherence to the vaginal walls. Often, this is believed to be due to their water miscibility and/or their lack of physical stability at 37 degrees C. (body temperature). Further, the nature of the active/therapeutic agent itself can cause the delivery system to deteriorate. This may be due to the fact that the active/therapeutic agent possesses surface active properties or obtains surface active characteristics when placed into various delivery systems known in the art. Examples of vaginal delivery systems, can be found in U.S. Pat. Nos. 5,055,303 and 5,266,329, both of which are incorporated herein by reference in their entirety.

Many known systems exhibit limited effectiveness since they rapidly release their active agents in an uncontrolled manner and rapid manner. Further, conventional systems also result in a relatively high systemic absorption of the active agent, which may be due in part to the instability of the system. This level of systemic absorption is such that in a plasma concentration versus time curve will result in an area under the curve (AUC) of at least about 200 ng/mL·hr. Typically, the AUC will be much higher, e.g., at least about 300 to as much as 4,500 ng/mL·hr. Further, conventional dosage forms are frequently discharged as an offensive leakage and drippage along with the minute vaginal secretions that are a normal physiological function. One particular clindamycin phosphate vaginal formulation currently known in the art is sold as Cleocin® and manufactured by Pharmacia & Upjohn.

The pharmacology of clindamycin is known in the art. See for example, Aroutcheva, A., et al., *The inhibitory effect of clindamycin on Lactobacillus in vitro., Infectious diseases in Obstetrics and Gynecology,* 9, 2001, (4), 239-44; and Muli, F., et al., *Use of continuous-culture biofilm system to study the antimicrobial susceptibilities of Gardnerella vaginalis and Lactobacillus acidophilus., Antimicrobial agents and chemotherapy,* 42, June 1998, (6) 1428-32, both of which are incorporated herein by reference in their entirety.

The toxicology of clindamycin is also well known in the art. See for example, Gray, J. E., et al., *The Oral Toxicity of Clindamycin in Laboratory Animals., Toxicology and Applied Pharmacology* 21, 1972, 516-531; and Bollert, J. A., et al., *Teratogenicity and Neonatal Toxicity of Clindamycin 2-Phosphate in Laboratory Animals., Toxicology and Applied Pharmacology* 27, 322-329, both of which are incorporated herein by reference in their entirety.

A controlled release system delivers the active agent to the site of action, activity, expected activity, absorption or use in a predetermined manner. This contrasts with conventional immediate release systems, which require frequent repetitive dosing in order to achieve the desired level of active agent. An unexpected advantage of a controlled release system is that the drug is administered fewer times a day or fewer times during the therapy period than conventional systems since the drug level in the vaginal cavity is maintained at a constant or controlled level. Unfortunately, the controlled release systems known in the art do not affect the total number of days that are required to treat a condition.

The present invention is advantageous because it provides a system for the delivery of an active agent in a controlled manner in the vaginal cavity for an extended period of at least several days. The vaginal drug delivery system may take the form of a multi-phase liquid or semi-solid, which is easily introduced into the vaginal cavity. Additionally, due to the bioadhesive nature of the delivery system, the material introduced into the vaginal cavity does not seep or seepage is reduced from this body cavity in an offensive manner. In comparison to conventional vaginal drug delivery with conventional creams and ointments, the present technology is further advantageous in that it reduces the number of administrations needed to obtain efficacy for active agents such as, clindamycin phosphate. The conventional clindamycin phosphate vaginal cream (Cleocin™ Vaginal Cream) needs to be administered nightly for 7 consecutive nights in order to affect a cure. The present technology needs to be administered only once to affect the same cure.

Besides advantages regarding the convenience afforded by a single dose administration, the present technology is also characterized with providing a highly cost effective treatment for vaginal infections in that only one applicator is needed to do the treatment as contrasted to 7 applicators needed for the conventional cream product. Additionally, since only 100 mg of active drug (2% of a 5.0 gram application) is needed with the present technology, as compared to 700 mg of active drug required for a full dose of therapy with the conventional cream (2% of 5.0 gram times 7 applications) a significant savings in active drug and excipients is also achieved.

SUMMARY OF THE INVENTION

The present inventive subject matter is directed to a pharmaceutical formulation to treat vaginal conditions in a human patient comprising: an effective amount of at least one active agent; a modified release dosage form which provides modified release of said active agent or agents upon vaginal administration to said patient; and wherein said formulation, when containing a total dose of each active agent of about 25 µg to about 500 mg based on said active agent will produce a plasma concentration versus time curve (ng/ml versus hours) having an area under the curve (AUC) of less than about 600 ng·/mL·hr; and wherein the at least one active agent is selected from the group consisting of antibacterial agents, antiviral agents, spermicides, hormone agents, growth enhancing agents, cytokines, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents such as pH modifiers, and mixtures and combinations thereof.

The present inventive subject matter is further drawn to a pharmaceutical formulation comprising: an active pharmaceutical having surfactant properties; an emulsion comprising at least two phases, one phase comprises an external lipoidal phase and the other phase comprising an internal non-lipoidal phase wherein said lipoidal phases is continuous and the said non-lipoidal phase comprises at least 70% by volume of said emulsion; one or more primary stabilizing surfactants selected from the group consisting of phospholipid, non-ionic ester and mixtures thereof; and when said stabilizing surfactants is a phospholipid then one or more auxiliary stabilizing surfactants are added and when said stabilizing surfactants is a non-ionic ester then optionally one or more auxiliary stabilizing surfactants are added.

Still further, the present inventive subject matter is directed to A composition for treating a vaginal infection, comprising: an effective amount of at least one active agent; a modified release dosage form which provides modified release of said active agent or agents upon vaginal administration to said patient; and wherein said formulation, when containing a total dose of each active agent of about 25 µg to about 500 mg based on said active agent will produce a plasma concentration versus time curve (ng/ml versus hours) having an area under the curve (AUC) of less than about 600 ng/mL·hr; and wherein the at least one active agent is selected from the group consisting of antibacterial agents, antiviral agents, spermicides, hormone agents, growth enhancing agents, cytokines, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents such as pH modifiers, and mixtures and combinations thereof; and wherein said composition is administered in a single administration and is statistically equivalent to seven doses of a conventional clindamycin vaginal cream, 2% in the treatment of bacterial vaginosis.

Yet further, the present inventive subject matter is drawn to a pharmaceutical formulation to treat vaginal conditions in a human patient comprising: an effective amount of at least one active antibacterial agent; a modified release dosage form for vaginal administration to said patient; wherein said active antibacterial agent is not an antifungal agent; and wherein said formulation, when containing a total dose of each active antibacterial agent of about 25 µg to about 500 mg based on said active agent will produce a plasma concentration versus time curve (ng/ml versus hours) having an area under the curve (AUC) of less than about 600 ng/mL·hr.

Another embodiment of the present inventive subject matter is drawn to a pharmaceutical formulation to treat vaginal conditions in a human patient comprising: an effective amount of at least one active antibacterial agent; a modified release dosage form for vaginal administration to said patient; wherein said active antibacterial agent is not an antifungal agent; wherein said antifungal agent is not butaconazole; and wherein said formulation, when containing a total dose of each active antibacterial agent of about 25 µg to about 500 mg based on said active agent will produce a plasma concentration versus time curve (ng/ml versus hours) having an area under the curve (AUC) of less than about 600 ng/mL·hr.

A further embodiment of the present inventive subject matter is directed to a method of stabilizing a clindamycin formulation by adding one or more primary stabilizing surfactants selected from the group consisting of a phospholipid, a non-ionic ester, and mixtures thereof; wherein when said stabilizing surfactant is a phospholipid, then one or more auxiliary stabilizing surfactants are added, and when said stabilizing surfactant is a non-ionic ester, then optionally one or more auxiliary stabilizing surfactants are added.

An even further embodiment of the present inventive subject matter is drawn to a method of treating or preventing a reoccurrence of a vaginal infection in a patient comprising administering a single dose of a pharmaceutical formulation comprising an active pharmaceutical having surfactant properties to a patient in need thereof effective to treat said vaginal condition.

An additional further embodiment of the present inventive subject matter is drawn to a method of treating a vaginal infection by administering a pharmaceutical formulation for vaginal administration comprising: an effective amount of at least one active agent; a modified release dosage form which provides modified release of said active agent or agents upon vaginal administration to said patient; and wherein said formulation, when containing a total dose of each active agent of about 25 µg to about 500 mg based on said active agent will produce a plasma concentration versus time curve (ng/ml versus hours) having an area under the curve (AUC) of less than about 600 ng/mL·hr; and wherein the at least one active agent is selected from the group consisting of antibacterial agents, antiviral agents, spermicides, hormone agents, growth enhancing agents, cytokines, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents such as pH modifiers, and mixtures and combination thereof; and wherein said administration is a single administration and is statistically equivalent to seven doses of a conventional clindamycin vaginal cream, 2% in the treatment of bacterial vaginosis.

Further still an embodiment is drawn to method for treating vaginal conditions, which comprises: administering topically to a vaginal mucosal tissue site a modified release pharmaceutical formulation comprising at least one active agent, wherein the formulation maintains topical residence in a vaginal cavity for up to 10 days; and wherein systemic absorption of the at least one active agent is minimized.

Yet another embodiment is drawn to a method for treating vaginal conditions, which comprises: administering topically to a vaginal mucosal tissue site a modified release pharmaceutical formulation comprising at least one active agent, wherein the formulation maintains topical residence in a vaginal cavity for up to 7 days; and wherein systemic absorption of the at least one active agent is minimized.

Still a further embodiment is drawn to a method of reducing adverse effects of an active pharmaceutical ingredient formulation comprising administering to a patient in need thereof a pharmaceutical formulation comprising an active pharmaceutical having surfactant properties to a patient in need thereof.

In currently available products, containing clindamycin phosphate for use intravaginally in the treatment of bacterial vaginosis, the common system of delivery is a semi-solid cream. The dosage form is conventional in that it consists of a continuous aqueous phase and a disperse non-aqueous phase. The active drug being solubilized, or dispersed in the aqueous phase which allows immediate contact of active pharmaceutical ingredients with surfaces which are in need of relief from microbial insult. It also allows dilution, rinsing and leakage of the product from these surfaces and does not allow the optimum contact time required to effectively impact the life cycle of those organisms which are infecting the surrounding tissues. Subsequent to this, multiple applications of the product 3 to 7 times a week are needed to provide relief and cure of the condition. The required repeated application of the active pharmaceutical ingredients (API's) using this system increases the potential for systemic uptake and also increases the likelihood of tissue irritation.

In order to increase the contact time of the API to be more effective against microorganisms and at the same time reduce the systemic uptake and irritation potential, the reduction of multiple doses is a desired strategy. In order to reduce the dosage requirement one must overcome the physical loss of the delivery system through dilution, rinsing or leakage caused by indigenous fluids and temperature. A system that will adhere to the mucosal surfaces and resist rinsing through aqueous fluids while at the same time release levels of the active pharmaceutical ingredient at a rate which will minimize systemic uptake but stay in contact with infected surfaces long enough to interfere with the infecting organisms life cycle would reduce the number of applications needed.

A system of this nature has been developed which provides vaginal delivery systems, which release an active agent to a site of absorption or action in a controlled manner and are bioadherent to the vaginal surfaces. This system which releases active agent to a site in a controlled manner for at least three hours and is bioadherent has a continuous phase that is lipoidal and a disperse or internal phase that is nonlipoidal and is described in U.S. Pat. No. 5,266,329. This system as described however, when used with a compound which exhibits surfactant-like behavior becomes physically unstable and loses the advantage of its bioadherent nature and resistance to wash off.

In order to overcome this destabilization one strategy is to add a surfactant which will counter-act or modify the influence of the API's behavior. Possible mechanisms targeted can be molecular structure, charge, orientation at the interface, effect on surface energies, solubility in either phase, shift in equilibrium of molecules absorbed at the interface, replacement of interfacial molecular populations, change in concentration. These variables are considered singly or in combination. The exact mechanisms are not completely understood; however, it is the effect of stabilization that the present formulations achieve. Our efforts unexpectedly focused on non-ionic surfactants and phospholipids used either alone or in combination with formulations that were stable before the addition of the API.

It has been unexpectedly found that phospholipids in combination with surfactants from a system previously destabilized with Clindamycin phosphate became physically stable.

From physical observation of these initial formulations and the purity of the phospholipids initially used it was determined that the phospholipids composition needed refinement. It was found that phosphotidyl choline purified to a level of 90% produced an emulsion with optimum physical properties.

In addition to the surfactant combination containing phospholipids, surfactants were found which either alone or in combination produced the desired emulsion containing Clindamycin phosphate.

BRIEF DESCRIPTION OF THE DRAWINGS

FIG. 2 represents the therapeutic cure rate of an inventive formulation as compared to a known formulation.

FIG. 4 depicts the linear plot of mean plasma clindamycin concentrations versus time.

DESCRIPTION OF THE PREFERRED EMBODIMENTS

Figure 1:
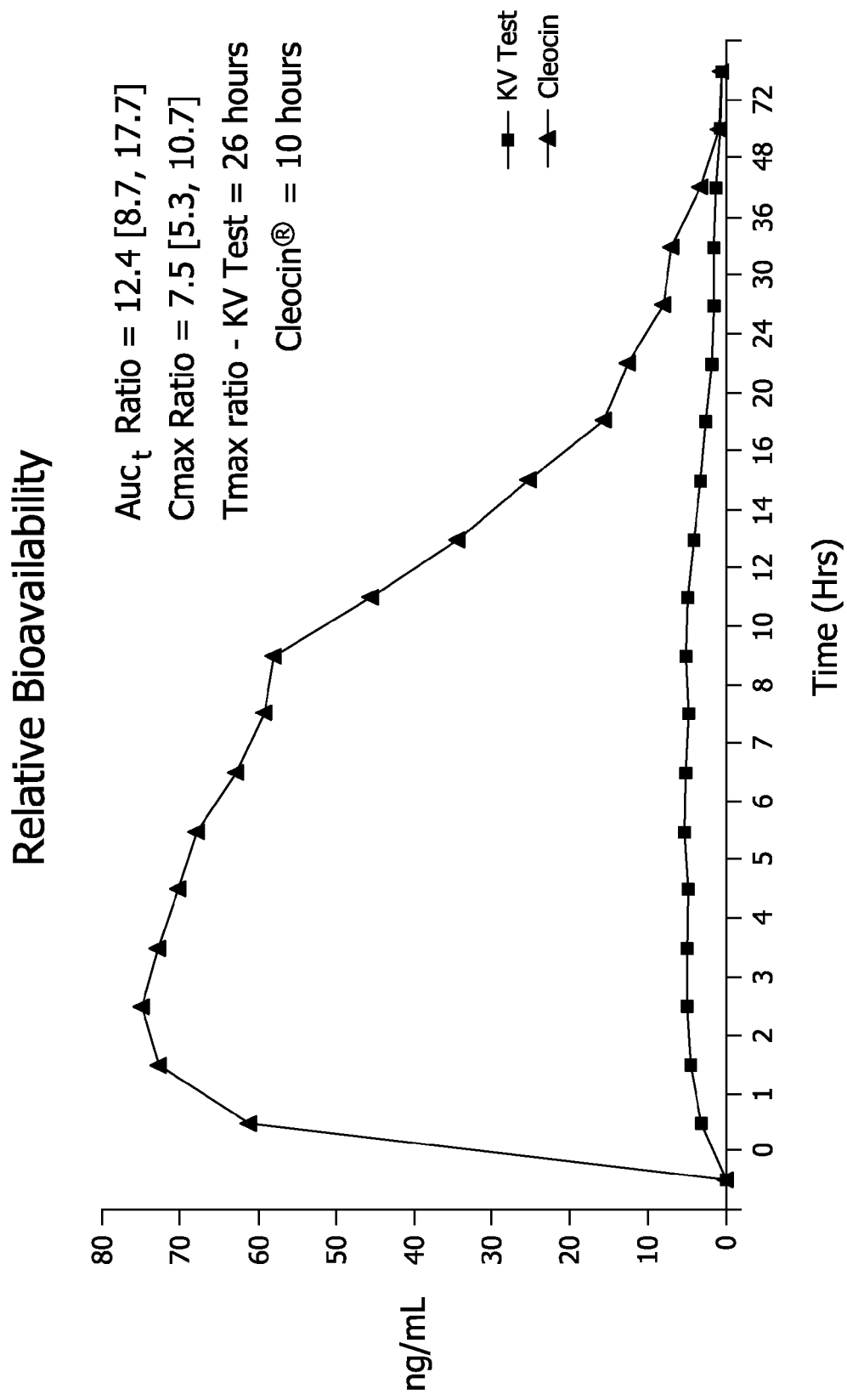
FIG. 1 represents the relative bioavailability of an inventive formulation over time as compared to a known formulation.

The purpose of the present invention is to stabilize known active agents that have surfactant-like properties in an emulsion form. The present invention is primarily directed to vaginal delivery systems and delivery systems which are effective upon mucosal tissues, such as those of the mouth, throat, nasal cavity, vulvovaginal and rectum. In the instance of vaginal delivery, the systems are characterized by their ability to deliver agents to a specific site in the vaginal cavity, in a controlled manner over a prolonged period of time. The systems are bioadherent to the epithelial tissue and are comprised of at least two phases. The systems when in a vaginal environment retain their integrity and display physical stability for an extended residence time within the vaginal cavity.

As discussed above, the vaginal cavity produces an aqueous environment conducive to the growth of bacteria, fungi, yeast and microorganisms. The known systems are not optimally effective for treating such conditions either due to their water miscability, lack of bioadhesion, or lack of physical stability in the vaginal environment of 37 degrees C. The vaginal cavity as defined herein not only includes the vagina, but also associated surfaces of the female urinary tract, such as, the ostium of the urethra. Delivery systems are a combination of nonactive ingredients which serve to solubilize, suspend, thicken, dilute, emulsify, stabilize, preserve, protect, color, flavor and fashion an active agent into an acceptable and efficacious preparation for the safe and convenient delivery of an accurate dose of said active agent.

The term "active agent" as used herein refers to agents selected from the group consisting of antifungal agents, antibacterial agents, antimicrobial agents, anti-infective agents, antiviral agents, spermicides, hormone agents, growth enhancing agents, cytokines, antitrichomonial agents, antiprotozoan agents, antimycoplasm agents, antiretroviral agents, nucleoside analogues, reverse transcriptase inhibitors, protease inhibitors, contraceptive agents, sulfadrugs, sulfonamides, sulfones, hygiene agents, probiotic agents, vaccine agents, antibody agents, peptide agents, protein agents, polysaccharide agents, nucleic acids, plasmids, liposomes, carbohydrate polymers, transgenic bacteria, yeast, chemotherapeutic agents, steroid agents, growth enhancing agents, libido enhancers, androgenic substances, chitin derivatives, environment modifying agents such as pH modifiers, and mixtures and combinations thereof.

Antibacterial agents are those agents which when administered have a therapeutically effective impact on bacterial growth. This impact may be to slow or inhibit such growth. Preferable antimicrobial agents are selected from the group consisting of clindamycin, clindamycin phosphate, clindamycin hydrochloride, salts thereof, complexes of clindamycin base and mixtures thereof. Antibacterial agents also include nitromidazoles, such as metronidazole, tinidazole, nimorazole, ornidazole, and benznidazole. Other compounds which have a mixed activity, which includes antibacterial activity, and are also considered antibacterials for use in the present invention. These include, but are not limited to, fenticonazole, ciclopirox, econazole, butenafine HCl, and nafimidone.

An additional aspect of the present invention involves the use of combinations of active agents that have surfactant properties and active agents that do not possess such properties. A non-limiting example of such a formulation could include an antibacterial active agent and an antifungal active agent, such as clindamycin along with butoconazole.

It is essential to the present inventive formulations that the delivery system not only release an active agent, but that it releases the agent in a controlled manner to a site of optimal absorption or action. That is, an agent is made available for absorption, pharmacological or other effect at a site of absorption or action, in an amount sufficient to cause a desired response consistent with the intrinsic properties of the agent and which provides for maintenance of this response at an appropriate level for a desired period of time. Thus, the systems described herein are characterized by the controlled release of an active substance from a delivery system at a receptor site, site of action, site of absorption, or site of use and the achievement of the desired effect at that site. The systems of the invention are not miscible in water and are not harmful for use in the vaginal cavity.

Of note in the present system is the fact that long term, modified, controlled and/or sustained release can be affected over a long period of time, at least about 24 hours to about 96 hours and as long as 7 to 10 days, through the administration of a low number of doses. In some cases as little as one dose can be administered to cover a treatment period of a number of days. Doses may be given once daily, multiple daily doses, every other day, every two, three, four days, etc., are within the scope of this invention. Alternatively, for treating recurring conditions, administration on the first and fourth days are feasible.

Not only does the present system have the ability to deliver an active pharmaceutical ingredient, i.e., an active agent, over an extended period of time, but the active agent will retain a relatively low plasma concentration (C max) throughout the administration. For example, a plasma concentration achieved with a single dose of 2% clindamycin may be about 1.000 to about 40.000 ng/mL. Further, in comparing the plasma concentration versus time (ng/mL versus hours), the area under curve (AUC) may be determined and will generally remain below about 1,341.76 ng/mL·hr. Typically, the AUC is less than 600 ng/mL·hr, and for example can be between about 25 and 350 ng/mL·hr. Both the plasma concentration and the area under curve displayed by the present product are lowered as opposed to the known formulations.

The systems are comprised of unit cells. These unit cells are the basic, nondivisible, repeating units of the system. The unit cells have internal and external phases, which represent the internal and external phases of the systems. The systems may be described in conventional classifications, such as emulsions, emulsions/dispersion, double emulsions, suspensions within emulsions, suppositories, foams, creams, ovules, inserts, and etc. The systems are usually in the form of emulsions either of medium or high internal phase ratio, preferably greater than 70% and more preferably greater than 75% by volume. The delivery systems are liquids or semi-solids with viscosities that range from 5,000 to one million centipoise, preferably 100,000 to 800,000 centipoise. The systems in order to adhere to the vaginal cavity must have sufficient viscosity to retain their integrity.

The unit cells have an internal phase which may be discontinuous and which is nonlipoidal. The nonlipoidal character of the phase renders it miscible with water. Preferably the internal phase comprises water, glycerine, sorbitol solutions or combinations thereof. Generally, it is desirable that the internal phase be of high osmotic pressure. The internal phase may be multiphasic and may be a solution, suspension, emulsion or combination thereof and it contains at least a portion of the active agent. Also, the internal phase may contain suspended solids, emulsions, osmotic enhancers, extenders and dilutants, as well as fragrances, colors, flavors, and buffers.

The resistance of a solution to changes in hydrogen ion concentration upon the addition of small amounts of acid or alkali is termed buffer action. A solution which possesses such properties is known as a buffer solution. It is said to possess reserve acidity and reserve alkalinity. Buffer solutions usually consist of solutions containing a mixture of a weak acid and it's sodium or potassium salt or of a weak base and it's salt. A buffer then is usually a mixture of an acid and it's conjugate base.

The solution containing equal concentrations of an acid and it's salt, or a half-neutralized solution of the acid, has maximum buffer capacity. Other mixtures also possess considerable buffer capacity, but the pH will differ slightly from the half-neutralized acid.

The preparation of a buffer solution of a definite pH is a relatively simple process if the acid (or base) of appropriate dissociation constant is found. Small variations in pH are obtained by variations in the ratio of the acid to the salt concentration according to the equation:

$$pH = pk_a + \log [salt]/[acid]$$

The vaginal cavity exhibits an aqueous environment containing secreting glands whose fluids create an acidic pH in the range of 4.5 to 5.5. Therefore, in order to generate a buffer solution which has a pH of approximately 4.5, an acid with a $pk_a$ of approximately this value would be needed. Monoprotic acetic acid, for example, has a $pk_a$ value of 4.74 and the first two ionizable protons from citric acid have values of 3.13 and 4.76 respectively. Lactic acid is another example with a $pk_a$ of approximately 3.9.

While theoretical amounts of an acid and salt can be derived from the equation above, in a formulation that is a complicated mixture of many dissolved species it is more practical to titrate a given amount of an acid, typically citric acid or acetic acid, with a solution of known concentration of either sodium or potassium hydroxide until the desired pH value is obtained in the actual formulation.

The unit cells also have an external phase. This phase is lipoidal and is the continuous phase of the systems. The term lipoidal pertains to any of a group of organic compounds comprising the neutral fats, fatty acids, waxes, phosphatides, petrolatum, fatty acid esters of monoprotic alcohols and mineral oils having the following common properties: insoluble in water, soluble in alcohol, ether, chloroform or other fat solvents, and which exhibit a greasy feel. Examples of oils suitable for use in these delivery systems are mineral oils with viscosities of 5.6 to 68.7 centistokes, preferably 25 to 65 centistokes, and vegetable oils illustrated by coconut, palm kernel, cocoa butter, cottonseed, peanut, olive, palm, sunflower seed, sesame, corn, safflower, rape seed, soybean and fractionated liquid triglycerides of short chain (naturally derived) fatty acids. This external phase may also contain fragrances, colors, flavors, and buffers. Of specific interest in the external phase is the use of phospholipids or non-ionic esters which stabilize the system, prevent phase separation and may impart little to no color on the resultant product. Refined forms of lecithin are particularly preferred in this regard. While not being bound by any particular theory, it is believed that refined lecithins may act to reside at the oil and water interface point in order to impart stability, especially in systems containing drugs having surfactant properties, which may disrupt the oil and water interface. This stability may be due to increased attraction between molecules within the interface, and a physical barrier created thereby protecting the interface from the surfactant drug. Refined lecithins may have a very high percentage of phosphatidylcholine, wherein the charged end of the molecule is large in comparison to other phosphatides. Due to phosphatidylcholine's hydrophilic nature, it is also possible that they become partially solubilized in the aqueous phase side of the system interface while the lipid end of the molecule is anchored in the oil phase. Thus, the large hydrophilic end of the molecule may provide the barrier to the absorption of active ingredients having surfactant qualities. Preferably, the refined lecithin will contain not less than about 70% phosphatidylcholine and, more preferably, not less than about 80%. The refined lecithin may contain as much as about 96% phosphatidylcholine. Typically, food grade lecithin is not acceptable, but may be used when the formulation is modified by means known to one of ordinary skill in the art. Phospholipon 90, manufactured by the American Lecithin Company, is a preferred refined lecithin according to the present invention.

The active agent may be any of those which are approved for or used for the treatment, prophylaxis, cure or mitigation of any disease of the vagina, urinary tract, cervix or other female reproductive organ or inducement of conception; for aesthetic or cosmetic usage, for diagnostic purposes; for systemic drug therapy; or for sex determination of offspring. The agent must have utility when administered by delivery to all or a portion of the vaginal surfaces. Potential agents are normally well-known due to their need for governmental approval or common usage. At least a portion of the active agent must usually be contained in the internal phase in order to obtain the release characteristics of the systems.

It has been found that when active agents including antibiotics, such as, clindamycin, are used as part of the active agent, the conventional treatment period or quantity of agent used is reduced by at least 25%. Normally a controlled release drug system reduces the number of times a day that a drug must be administered. However, it does not affect the overall length of treatment. With respect to certain active agents it has been discovered that the drug delivery system described herein reduces the treatment period by at least 25%. Tests utilizing clindamycin upon bacterial vaginitis, e.g., *Gardnerella* morphotype, have demonstrated this unexpected result. It is believed that this effect can be achieved with other antibacterial agents and antifungal agents. Thus, the treatment of microbes can be achieved in much shorter time or with substantially less drug with the system of the invention.

Adjacent unit cells have common external phases. The external phase of the unit cells provides the continuous phase of the system. The unit cells may utilize emulsifiers. Preferably, the emulsifiers are soluble in the lipoidal or external phase. Suitable emulsifiers are those oil miscible, surface active compounds which are acceptable for use in foods, pharmaceuticals, and/or cosmetics. Examples of such emulsifiers are low molecular weight polyglycerols, which have been esterified with fatty acids or fatty acid esters, or mono and diglyceride mixtures alone or with the addition of metallic soaps, such as, aluminum stearate. The metallic soaps appear to improve the characteristics of some of the emulsions.

The systems can be introduced into the vaginal cavity by the use of conventional applicators or other coating or spraying means. Although the systems are deformable at physiological temperatures, approximately 37 degrees C., they do not lose integrity in the same manner as the known systems. The present delivery systems, unlike known systems, are not characterized by offensive leakage from the vaginal cavity following the insertion of the system. Since the present systems break down over an extended period, nonaqueous components are either absorbed or released from the vaginal cavity at an unnoticeable rate, which makes no significant increase in normal secretions.

The characteristics of these systems are a result of their inherent integrity under vaginal conditions. The systems release the active agent in the vaginal cavity due to diffusion of the active agent, rupture of the unit cells and/or a combination of these two mechanisms. This release of active agent can be linear or non-linear depending on the composition of the system. Factors which effect the release rate are the percentage of active agent contained in each of the phases; and the type of system, such as, emulsion, double emulsion, suspension; thickness of the external membrane; amount and nature of emulsifier in the external phase; osmotic pressure of the internal phase; pH of the internal phase; diffusibility of the active species through the external phase membrane; etc. Within the physiological environment of the vaginal cavity all of the chemical and physical forces present, including fluids, enzymes, pH, chemical balance, temperature, and shear forces from body movement, affect the rate of breakdown of the system. These forces are not believed to destroy the integrity of the systems at the same rate as other known systems.

The systems may be prepared by well-known continuous or batch processes. When processing using conventional emulsions, shear force is applied to the system components by use of homogenizers, mills, impingement surfaces, ultrasound, shaking or vibration. Unlike conventional emulsions, the mixing shear should be at low levels in order to prevent destruction of the system resulting from excess energy used in the process. Temperature is not usually a critical factor in the preparation of the systems. The temperatures utilized will be dependent upon the final end product desired. Phase combination is usually performed at ambient temperatures.

The systems may be prepared by mixing the internal with the external phase in a planetary-type mixer with sweep blade with counter-rotating mixer by pumping the aqueous phase into the oil phase. Another manner of preparing the system is by use of a continuous mixer, which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary, depending upon the product produced as will the rate of flow of the two phase streams. In some preparations, both methods are used. The emulsion is prepared in the planetary-type with sweep blade with the counter-rotating mixer. The emulsion is the pumped through the continuous mixer to increase emulsion viscosity.

Depending upon the characteristics, such as solubility, etc., of the active pharmaceutically active ingredient, the active ingredient may be added in either the aqueous or oil phase. In either case, the active ingredient may be added into the appropriate phase to preserve its therapeutic nature and activity. Where the active is both water and oil soluble or minimally water and/or soluble, the active may be dispersed in the phase resulting in the most physically and chemically stable product or results in the cost effective and/or simplified production process.

The following examples are illustrative of preferred embodiments of the invention and are not to be construed as limiting the inventive subject matter thereto. All polymer molecular weights are mean average molecular weights. All percentages are based on the percent by weight of the final delivery system or formulation prepared unless otherwise indicated and all totals equal 100% by weight:

Example 1

This example demonstrates the preparation of a formulation according to the present inventive subject matter.

|  | Wt % |
| --- | --- |
| Water, purified, USP | 45.3 |
| Sorbitol Solution | 36.8 |
| Edetate Disodium, USP | 0.05 |
| Clindamycin Phosphate, USP | 2.80 |
| Mineral Oil, USP | 7.00 |
| Polyglyceryl-3-Oleate | 2.70 |
| Glycerol Monoisostearate | 2.70 |
| Lecithin, Phospholipon 90G | 1.00 |
| Silicon Dioxide, Hydrophobic | 1.00 |
| Microcrystalline Wax, NF | 0.40 |
| Methylparaben, NF | 0.20 |
| Propylparaben, NF | 0.05 |

| Analysis: | target | Result |
| --- | --- | --- |
| Clindamycin | 20 mg/g | 104% of target |
| Methylparaben | 2.0 mg/g | 97.5% of target |
| Propylparaben | 0.5 mg/g | 96.9% of target |
| Viscosity | in process | 860,000 cps |

NB: The amount of active ingredient and water to be added is calculated per batch based upon the assay and water content of the raw materials.

General Method of Preparation (Scale-Up/Submission Batch)

Aqueous Phase Preparation

1. The following items are loaded into a stainless steel mixing tank equipped with a cover and variable speed mixer and mixed at room temperature until all solids are dissolved: At this time after water and sorbitol are mixed if buffers are used i.e., citrate salts or others, they are added to the solution and dissolved Water, Purified
Sorbitol Solution
Edetate Disodium 2. Clindamycin Phosphate is added to this solution and mixed until dissolved.

Oil Phase Preparation

3. The following items are loaded into a stainless steel jacketed kettle equipped with a sweep blade and variable speed mixer and mixed at 70-75° C. until all solids are dissolved:

Mineral Oil
Polyglyceryl-3-Oleate
Glyceryl Monoisostearate
Microcrystalline Wax

4. A portion of the material from Step 3 is drained from the kettle and placed in a smaller stainless steel container. Then Phospholipon 90G is added and the mixture is stirred at 80-85° C. until the Phospholipon 90G is completely dissolved.

5. After the Phospholipon 90G has dissolved, the solution from Step 4 is returned to the kettle of Step 3 and Methylparaben and Propylparaben are added and dissolved at 70-75° C.

6. While mixing Silicon Dioxide, Hydrophobic is added to the kettle and mixed to create an initial dispersion.

7. While mixing, the material from Step 6 is transferred through a colloid mill into a stainless steel jacketed kettle equipped with counter rotation blade and sweep blade.

Phase Combination

8. While mixing the oil phase from Step 7 the aqueous phase from Step 2 is added in a controlled fashion by means of a transfer pump until phase addition is complete. Mixing is then continued for a predetermined period of time to establish the preliminary emulsion.

9. The preliminary emulsion is then transferred by means of a transfer pump through a secondary mixing chamber at pre-established flow rates and mixing speeds in order to achieve final viscosity.

10. The material is then transferred into bulk containers for packaging into individual applicators.

Example 2

| Water, purified, USP | 41.978 |
| Sorbitol Solution | 39.600 |
| Edetate Disodium, USP | 0.0500 |
| Clindamycin Phosphate, USP | 2.6900 |
| Mineral Oil, USP | 10.000 |
| PEG-30 Dipolyhydroxystearate | 5.0000 |
| Microcrystalline Wax, NF | 0.4250 |
| Methylparaben, NF | 0.1800 |
| Propylparaben, NF | 0.0500 |

| Analysis: | target | Result |
|---|---|---|
| Clindamycin | 20 mg/g | 76.8% of target |
| Methylparaben | 2.0 mg/g | 98.5% of target |
| Propylparaben | 0.5 mg/g | 96.5% of target |
| Viscosity | initial | 224,000 cps |

NB: The amount of active ingredient and water to be added is calculated per batch based upon the assay and water content of the raw materials.

The formulation was prepared in accordance the general methodology provided herein.

Example 3

| Water, purified, USP | 45.23 |
| Sorbitol Solution | 30.00 |
| Edetate Disodium, USP | 0.250 |
| Clindamycin Phosphate, USP | 2.690 |
| Mineral Oil, USP | 8.000 |
| Sorbitan Monoisostearate | 8.000 |
| Sorbitan Monostearate | 4.000 |
| Silicon Dioxide, Hydrophobic | 1.000 |
| Microcrystalline Wax, NF | 0.600 |
| Methylparaben, NF | 0.180 |
| Propylparaben, NF | 0.050 |

| Analysis: | target | Result |
|---|---|---|
| Clindamycin | 20 mg/g | 101% of target |
| Methylparaben | 2.0 mg/g | 99.9% of target |
| Propylparaben | 0.5 mg/g | 100.7% of target |
| Viscosity | initial | 400,000 cps |

NB: The amount of active ingredient and water to be added is calculated per batch based upon the assay and water content of the raw materials.

The formulation was prepared in accordance with the general methodology provided herein.

Example 4

The formulations of Example 4 cover a citrate buffered clindamycin, a citrate buffered metronidazole and a non-buffered metronidazole. These formulations can be prepared according to the process as set forth in Example 1.

Such formulations would be expected to administer therapeutic effective amounts to patients being treated.

| Buffered Clindamycin | |
|---|---|
| Water, purified, USP | 45.300 |
| Sorbitol Solution, USP | 36.100 |
| Edetate Disodium, USP | 00.050 |
| Citric Acid USP anhydrous | 00.490 |
| Potassium Hydroxide | 00.240 |
| Clindamycin Phosphate, USP | 2.800 |
| Mineral Oil, USP | 7.000 |
| Polyglyceryl-3-oleate | 2.700 |
| Glycerol Monoisostearate | 2.700 |
| Lecithin, Phospholipon 90G | 1.000 |
| Silicon Dioxide, Hydrophobic | 1.000 |
| Microcrystalline Wax, NF | 0.400 |
| Methylparaben, NF | 0.200 |
| Propylparaben, NF | 0.050 |
| Buffered Metronidazole | |
| Water, purified, USP | 42.810 |
| Sorbitol Solution, USP | 40.149 |
| Edetate Disodium, USP | 00.250 |
| Citric Acid USP anhydrous | 00.490 |
| Potassium Hydroxide | 00.230 |
| Metronidazole, USP | 0.750 |
| Mineral Oil, USP | 8.032 |
| Sorbitan Monoisostearate | 4.000 |
| Sorbitan Tristearate | 1.426 |
| Silicon Dioxide, Hydrophobic | 1.013 |
| Microcrystalline Wax, NF | 0.600 |
| Methylparaben, NF | 0.200 |
| Propylparaben, NF | 0.050 |
| Non-Buffered Metronidazole | |
| Water, purified, USP | 42.810 |
| Sorbitol Solution, USP | 40.869 |
| Edetate Disodium, USP | 00.250 |
| Metronidazole, USP | 0.750 |
| Mineral Oil, USP | 8.032 |
| Sorbitan Monoisostearate | 4.000 |
| Sorbitan Tristearate | 1.460 |
| Silicon Dioxide, Hydrophobic | 1.013 |
| Microcrystalline Wax, NF | 0.600 |
| Methylparaben, NF | 0.200 |
| Propylparaben, NF | 0.050 |
| Microcrystalline Wax, NF | 0.400 |

Example 5

| Water | 41.310 |
| Sorbitol 70% | 40.869 |
| EDTA, disodium, USP | 00.250 |
| Metronidazole | 00.750 |
| Gloria Mineral Oil, USP | 8.032 |
| Hydrogenated Castor Oil | 1.500 |
| Sorbitan Monoisostearate | 4.000 |
| Sorbitan Monostearate | 1.426 |
| Hydrophobic Silicone Dioxide | 1.013 |

-continued

| | |
|---|---|
| Microcrystalline Wax | 0.600 |
| Methylparaben, NF | 0.200 |
| Propylparaben, NF | 0.050 |

The formulation was prepared in accordance with the general methodology provided herein.

Example 6

| | |
|---|---|
| Water | 41.310 |
| Sorbitol 70% | 40.869 |
| EDTA, disodium, USP | 00.250 |
| Metronidazole | 00.750 |
| Gloria Mineral Oil, USP | 8.032 |
| Beeswax, NF | 1.500 |
| Sorbitan Monoisostearate | 4.000 |
| Sorbitan Monostearate | 1.426 |
| Hydrophobic Silicone Dioxide | 1.013 |
| Microcrystalline Wax | 0.600 |
| Methylparaben, NF | 0.200 |
| Propylparaben, NF | 0.050 |

The formulation was prepared in accordance with the general methodology provided herein.

Example 7

| | |
|---|---|
| Water | 41.881 |
| Sorbitol 70% | 35.869 |
| EDTA, disodium, USP | 00.250 |
| Metronidazole | 00.750 |
| Gloria Mineral Oil, USP | 7.000 |
| Petrolatum | 6.000 |
| Sorbitan Monoisostearate | 5.000 |
| Sorbitan Monostearate | 1.400 |
| Hydrophobic Silicone Dioxide | 1.000 |
| Microcrystalline Wax | 0.600 |
| Methylparaben, NF | 0.200 |
| Propylparaben, NF | 0.050 |

The formulation was prepared in accordance with the general methodology provided herein.

Biological Data

The formulation of Example 1, as a clindamycin Vaginal Cream 2% was compared to Cleocin® Vaginal Cream 2%. Twenty healthy women received single 5 gm doses of the Example 1 and reference formulations according to a two-treatment, two-period, two-sequence randomized crossover design with a two-week washout between periods. Blood samples for measurement of plasma clindamycin concentration were collected before and 1, 2, 3, 4, 5, 6, 7, 8, 10, 12, 14, 16, 20, 24, 30, 36, 48, 72, and 96 hours after drug administration. Plasma concentrations of clindamycin were determined using a validated LC/MS/MS method with a lower limit of quantitation of 0.2 ng/mL.

Plasma concentrations and pharmacokinetic parameters after administration of both formulations were highly variable. Coefficients of variation for pharmacokinetic parameters ranged from 88% to 154% and 51% to 127% for the Example 1 and reference formulations. Mean plasma clindamycin concentrations after intravaginal administration of the Inventive cream formulation were substantially lower than those after administration of Cleocin® as were mean values for Cmax and the areas under the curve. The bioavailability of clindamycin from the Inventive cream formulation was 7.52% of that produced by Cleocin® based on Cmax and 12.4% of that produced by Cleocin® based on $AUC_{0-t}$ or $AUC_{\infty}$. See FIG. 1 for the results.

The results demonstrate that systemic exposure to clindamycin after intravaginal administration of the Inventive Vaginal Cream 2% was approximately 12% of that after administration of Cleocin® Vaginal Cream 2%.

The formulation of Example 1, namely clindamycin Vaginal Cream 2% was compared with the Cleocin® Vaginal Cream 2% in patients with bacterial vaginosis (BV). The study involved a multicenter, randomized, single-blind, parallel group study having 540 patients.

In the study, therapeutic cure was defined as having all 4 Amsel Criteria resolved (normal vaginal discharge, vaginal pH<4.7, <20% clue cells on wet mount, and negative "Whiff" test) and having a Nugent score less than 4 at study endpoint. The therapeutic cure rate was the primary efficacy outcome for patients in this study.

Figure 3:
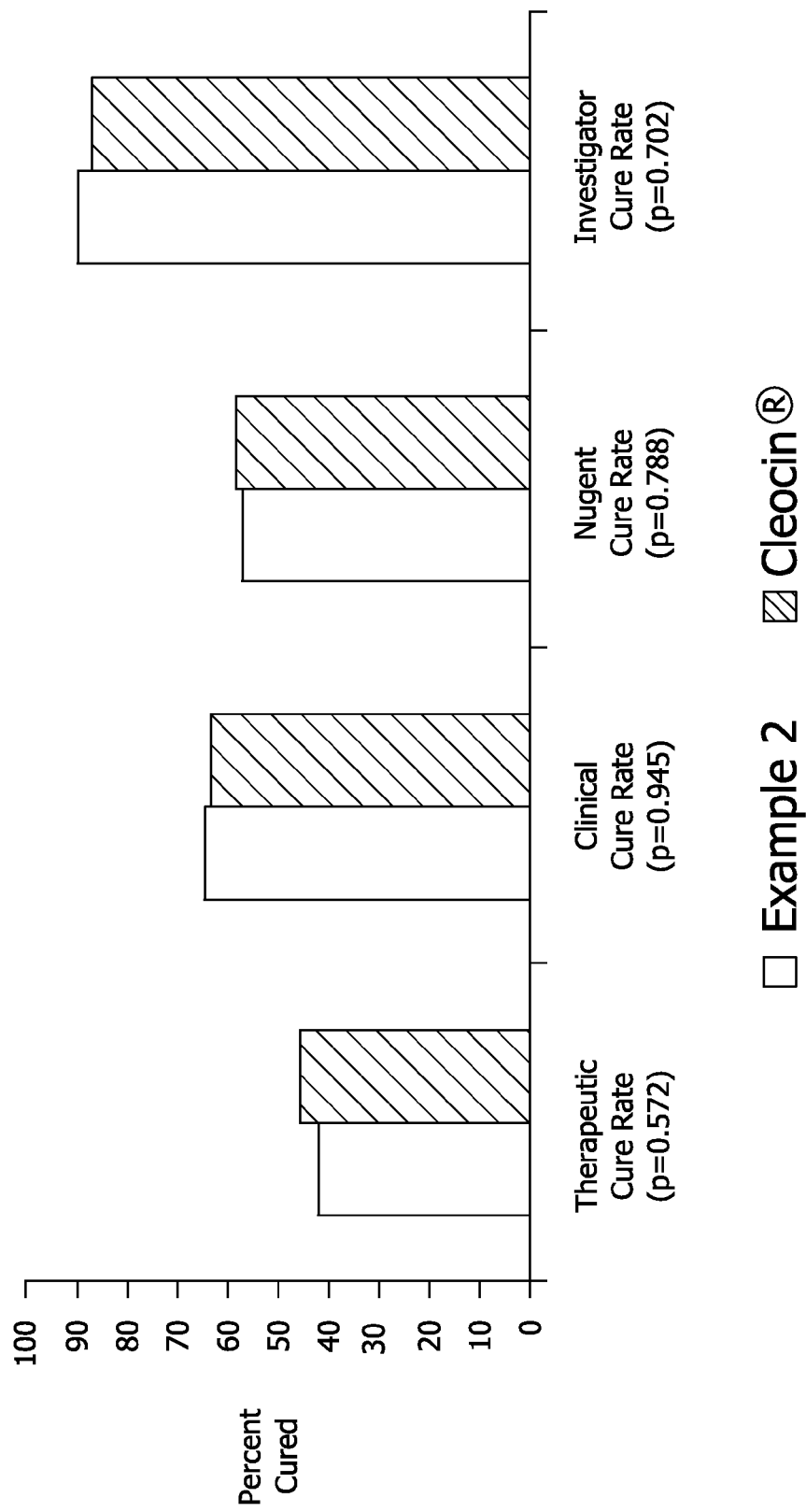
FIG. 3 depicts the primary and secondary efficacy outcomes per protocol population for an inventive formulation as compared to a known formulation.

The results of the study are set forth below and involve 1) The Therapeutic Cure Rate-See FIG. 2, and 2) The Primary and Secondary Efficacy Outcome—see FIG. 3.

The results of this study demonstrated that one dose of the formulation of Example 1 (clindamycin Vaginal Cream, 2%) was statistically equivalent to 7 doses of Cleocin® vaginal cream, 2% in the treatment of bacterial vaginosis based on therapeutic cure rate for all analysis populations (Per Protocol, modified Intent-to-Treat, and Intent-to-Treat).

Regarding the additional efficacy rates, Clinical cure, Nugent cure, and Investigator cure rates demonstrated secondary efficacy outcomes in this study. Clinical cure was defined as having all 4 Amsel Criteria resolved at study endpoint. Nugent cure was defined as having a Nugent score less than 4 at study endpoint. Investigator cure was defined by the investigator answering "no" to the following question at study endpoint: "In your opinion, does the patient require additional treatment for BV at this time?" The results are set forth in FIG. 3.

In addition, results of this study demonstrated that one dose of the Inventive formulation was statistically equivalent to 7 doses of Cleocin® Vaginal Cream, 2% in the treatment of bacterial vaginosis based on Clinical cure, Nugent cure, and Investigator cure for all analysis populations (Per Protocol, modified Intent-to-Treat, and Intent-to-Treat).

The study also demonstrated that 1.8% of 600 patients receiving the Inventive formulation dosed over three days, as compared to 2.7% of 1,325 patients receiving Cleocin® Vaginal Cream, 2% dosed over seven days, discontinued therapy due to drug related adverse events.

What is claimed is:

1. A pharmaceutical formulation to treat vaginal conditions in a human patient comprising:
   an effective amount of clindamycin phosphate; and
   a modified release dosage form which provides modified release of said clindamycin phosphate upon vaginal administration to said patient;
   wherein said formulation, when containing a total dose of clindamycin phosphate of about 25 µg to about 500 mg based on clindamycin will produce a plasma concentration versus time curve (ng/ml versus hours) having an area under the curve (AUC) of less than about 600 ng/mL·hr; and
   wherein said dosage form comprises:
   a. an emulsion comprising an external lipoidal phase and an internal non-lipoidal phase wherein said lipoidal phase is continuous and said non-lipoidal phase comprises at least 70% by volume of said emulsion;
b. one or more lecithins as primary stabilizing surfactants; and
c. one or more auxiliary stabilizing surfactants.

2. The pharmaceutical formulation as recited in claim 1, wherein said clindamycin phosphate is present in an amount of less than about 5% weight/weight based on clindamycin.

3. The pharmaceutical formulation as recited in claim 1 further comprising an antifungal agent.

4. The pharmaceutical formulation as recited in claim 1 further comprising an acid buffered phase.

5. The pharmaceutical formulation as recited in claim 1, wherein said one or more lecithins are selected from the group consisting of lecithin, refined lecithin and mixtures thereof.

6. The pharmaceutical formulation as recited in claim 1 wherein said one or more lecithins contain less than about 96% phosphatidylcholine.

7. The pharmaceutical formulation as recited in claim 1 wherein said one or more lecithins contain about 90% phosphatidylcholine.

8. The pharmaceutical formulation as recited in claim 1, wherein said auxiliary stabilizing surfactants are selected from the group consisting of polyglycerol-3-oleate, glycerol monoisostearate and mixtures thereof.

9. The pharmaceutical formulation as recited in claim 1, wherein said auxiliary stabilizing surfactants are present in said pharmaceutical formulation in amounts of about 2 to 15% weight/weight.

10. The pharmaceutical formulation as recited in claim 1, wherein said one or more lecithins contain not less than about 80% phosphatidylcholine.

11. The pharmaceutical formulation as recited in claim 1, wherein said one or more lecithins contain not less than about 70% phosphatidylcholine.

12. The pharmaceutical formulation as recited in claim 1, wherein the auxiliary stabilizing surfactants comprise polyglycerol-3-oleate and glycerol monoisostearate.

13. The pharmaceutical formulation as recited in claim 12, wherein the polyglycerol-3-oleate and glycerol monoisostearate are each present at a concentration of about 2.7% weight/weight.

14. The pharmaceutical formulation as recited in claim 1, wherein the one or more lecithins are present in an amount of about 1% weight/weight.

15. The pharmaceutical formulation as recited in claim 13, wherein the one or more lecithins are present in an amount of about 1% weight/weight.

16. A method of treating a vaginal infection by administering a therapeutically effective amount of a pharmaceutical formulation to treat said vaginal condition comprising administering to said patient a formulation which accomplishes a biologic endpoint of claim 1;
wherein the pharmaceutical formulation comprises an effective amount of clindamycin phosphate and a modified release dosage form comprising:
a. an emulsion comprising an external lipoidal phase and an internal non-lipoidal phase wherein said lipoidal phase is continuous and said non-lipoidal phase comprises at least 70% by volume of said emulsion;
b. one or more lecithins as primary stabilizing surfactants; and
c. one or more auxiliary stabilizing surfactants.

17. A method of stabilizing a clindamycin phosphate formulation by adding one or more lecithins as primary stabilizing surfactants and one or more auxiliary stabilizing surfactants.

* * * * *